United States Patent
Ravn et al.

(10) Patent No.: US 8,653,024 B2
(45) Date of Patent: Feb. 18, 2014

(54) USE OF AMPS FOR TREATMENT OF UTI/CYSTITIS

(75) Inventors: Birgitte Thue Ravn, Karlslunde (DK); Karoline Sidelmann Brinch, Copenhagen NV (DK); Dorthe Hoej Sandvang, Slangerup (DK); Hans-Henrik Kristensen Hoegenhaug, Holte (DK); Dorotea Raventos Segura, Rungsted Kyst (DK); Soeren Neve, Lyngby (DK)

(73) Assignee: Adenium Biotech Aps, Copenhagen (DK)

( * ) Notice: Subject to any disclaimer, the term of this patent is extended or adjusted under 35 U.S.C. 154(b) by 348 days.

(21) Appl. No.: 12/959,946

(22) Filed: Dec. 3, 2010

(65) Prior Publication Data

US 2011/0144002 A1    Jun. 16, 2011

Related U.S. Application Data

(60) Provisional application No. 61/286,459, filed on Dec. 15, 2009.

(30) Foreign Application Priority Data

Dec. 11, 2009   (EP) ..................................... 09178894

(51) Int. Cl.
    *A61K 38/17*    (2006.01)
    *C07K 14/435*   (2006.01)
    *A61P 31/04*    (2006.01)
    *A61P 29/00*    (2006.01)
    *A61P 13/02*    (2006.01)

(52) U.S. Cl.
    USPC .............................. 514/2.8; 514/2.3; 530/326

(58) Field of Classification Search
    USPC .......................................................... 530/326
    IPC ..................... A61K 38/17; C07K 14/435; A61P 31/04, 29/00, 13/02
    See application file for complete search history.

(56) References Cited

U.S. PATENT DOCUMENTS

2008/0214450 A1* 9/2008 Spodsberg ....................... 514/12

FOREIGN PATENT DOCUMENTS

WO    WO 2007/023163 A1    3/2007

OTHER PUBLICATIONS

Matthew E. Falagas, The Use of Intravenous and Aerosolized Polymixins for the Treatment of Infections in Critically Ill Patients: A review fo the Recent Literature, Mar. 31, 2006, Clinical Medicine and Research, vol. 4, No. 2:138-146.*
Liliana A. Haverson, Human Lactoferrin and Peptides Derived from a Surface-Exposed Helical Region Reduce Experimental *Escherichia coli* Urinary Tract Infection in Mice, Jul. 13, 2000, Infection and Immunity, vol. 68, No. 10:5816-5823.*
Neve S. Raventos, Novozymes A/S, An Arencicin-3 variant found by HTS screening of yeast libraries, Oct. 7, 2010, PPT poster.*
Milan Chromek, The Antimicrobial Peptide Cathelicidin Protects the Urinary Tract Against Invasive Bacterial Infection, Jun. 2006,Nature Medicine, vol. 12, No. 6:636-641.*
Tatiana V. Ovchinnikova, Recombinant Expression, Synthesis, Purification, and Solution Structure of Arenicin, Jun. 2007, Biochemical and Biophysical Research Communications, vol. 360, 156-162.*
Mare Cudic, In vitro and in vivo activity of an antibacterial peptide analog against uropathogens, May 15, 2003, Peptides, vol. 24, 807-820.*
Michael Zasloff, Antimicrobial Peptides, Innate Immunity, and the Normally Sterile Urinary Tract, 2007, J Am Soc Nephrol, vol. 18, 2810-2816.*
Khan et al., Biomedical Research, vol. 17, No. 3, pp. 179-181 (2006).
Merck, "Bacterial Urinary Tract Infections", Merck Manuals Online Medical Library, pp. 1-9 (2007).
Page et al., Current Opinion in Pharmacology, vol. 9, No. 5, pp. 558-565 (2009).
Sandvang et al., Abstracts of the Interscience Conference on Antimicrobial Agents and Chemotherapy, vol. 48, p. 326 (2008).

* cited by examiner

*Primary Examiner* — Julie Ha
*Assistant Examiner* — Erinne Dabkowski
(74) *Attorney, Agent, or Firm* — Cheryl H. Agris

(57) ABSTRACT

Provided is treatment of urinary tract infections including bladder infections caused by uropathogenic bacterial strains such as for example *Escherichia coli* with a beta-hairpin antimicrobial Arenicin polypeptide derived from the murine polychaeta *Arenicola marina*. Also provided are variants of Arenicin for treatment of urinary tract infections.

10 Claims, No Drawings

```
                        SEQUENCE LISTING

<160> NUMBER OF SEQ ID NOS: 3

<210> SEQ ID NO 1
<211> LENGTH: 21
<212> TYPE: PRT
<213> ORGANISM: Arenicola marina
<220> FEATURE:
<221> NAME/KEY: mat_peptide
<222> LOCATION: (1)..(21)

<400> SEQUENCE: 1

Gly Phe Cys Trp Tyr Val Cys Val Tyr Arg Asn Gly Val Arg Val Cys
1               5                   10                  15

Tyr Arg Arg Cys Asn
            20

<210> SEQ ID NO 2
<211> LENGTH: 21
<212> TYPE: PRT
<213> ORGANISM: Artificial sequence
<220> FEATURE:
<223> OTHER INFORMATION: Synthetic construct
<220> FEATURE:
<221> NAME/KEY: mat_peptide
<222> LOCATION: (1)..(21)

<400> SEQUENCE: 2

Gly Phe Cys Trp Asn Val Cys Val Tyr Arg Asn Gly Val Arg Val Cys
1               5                   10                  15

His Arg Arg Cys Asn
            20

<210> SEQ ID NO 3
<211> LENGTH: 21
<212> TYPE: PRT
<213> ORGANISM: Artificial sequence
<220> FEATURE:
<223> OTHER INFORMATION: Synthetic construct
<220> FEATURE:
<221> NAME/KEY: mat_peptide
<222> LOCATION: (1)..(21)
```

```
<400> SEQUENCE: 3

Gly Phe Cys Gly His Val Cys Val Tyr Arg Asn Gly Val Arg Val Cys
1               5                   10                  15

Tyr Arg Arg Cys Asn
                20
```

USE OF AMPS FOR TREATMENT OF UTI/CYSTITIS

CROSS-REFERENCE TO RELATED APPLICATIONS

This application claims priority or the benefit under 35 U.S.C. 119 of European application no. 09178894.3 filed Dec. 11, 2009 and U.S. provisional application No. 61/286,459 filed Dec. 15, 2009, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to the treatment of urinary tract infections with antimicrobial peptides.

2. Background

A urinary tract infection (UTI) is a bacterial infection that affects kidneys, ureter, bladder and urethra. The main causitive agent is uropathogenic strains of *Escherichia coli* (UPEC). Although urine contains a variety of fluids, salts, and waste products, it is usually sterile. When bacteria get into the bladder or kidney and multiply in the urine, they cause a UTI. The most common type of UTI is a bladder infection which is also often called cystitis, or bacterial cystitis. Another kind of UTI is a kidney infection, known as pyelonephritis, and is much more serious. Although they cause discomfort, most urinary tract infections can usually be quickly and easily treated with a short course of antibiotics.

However, increasing resistance in bacterial pathogens is a worldwide problem, and prevalence of antimicrobial resistance in patients with UTI is increasing. A study of 168 urine samples, which were collected from UTI patients, followed by isolation and identification of *E. coli* strains, showed that the majority of the isolates were resistant against four or more antibiotics (Khan and Zaman, "Multiple drug resistance pattern in Urinary Tract Infection patients in Aligarh", *Biomedical Research (India)* 17(3): 179-181 (2006)). Accordingly, there is a great need for novel antibiotics suitable for treatment of UTI, in particular UTI caused by multiple drug resistant *E. coli* strains.

It is an object of the present invention to provide polypeptides, which can be used for the treatment of urinary tract infections.

WO 2007/023163 disclosed Arenicin and methods of producing it.

SUMMARY OF THE INVENTION

We have now found that a particular group of antimicrobial peptides show excellent activity against urinary tract infections, and can be used in the treatment of urinary tract infections.

In a first aspect, the present invention provides the use of a polypeptide having antimicrobial activity, which comprises an amino acid sequence having at least 80% identity to the amino acid sequence of SEQ ID NO: 1, for the manufacturing of a medicament for therapeutic treatment of urinary tract infections.

In a second aspect, the present invention provides a polypeptide having antimicrobial activity, which comprises an amino acid sequence having at least 80% identity to the amino acid sequence of SEQ ID NO: 1, for use in the treatment of urinary tract infections.

In another aspect the present invention provides a method of treating urinary tract infections, comprising administering to a subject in need of such treatment an effective amount of a polypeptide having antimicrobial activity, which comprises an amino acid sequence having at least 80% identity to the amino acid sequence of SEQ ID NO: 1.

Urinary tract infections according to the present invention may be cystitis, such as bacterial cystitis. It may be caused by Gram negative bacteria, preferably an uropathogenic strain of *E. coli* (UPEC). In a preferred embodiment, the urinary tract infections are caused by multiple drug resistant *E. coli* strains.

A polypeptide for use according to the present invention, or for treating urinary tract infections according to the present invention, is designated hereinafter as "polypeptide(s) of (according to) the present invention".

DETAILED DESCRIPTION OF THE INVENTION

Definitions

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect, wherein the term "bactericidal" is to be understood as capable of killing bacterial cells. The term "bacteriostatic" is to be understood as capable of inhibiting bacterial growth, i.e., inhibiting growing bacterial cells. The term "fungicidal" is to be understood as capable of killing fungal cells. The term "fungistatic" is to be understood as capable of inhibiting fungal growth, i.e., inhibiting growing fungal cells. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

In a preferred embodiment, the term "antimicrobial activity" is defined as bactericidal and/or bacteriostatic activity. More preferably, "antimicrobial activity" is defined as bactericidal and/or bacteriostatic activity against *Escherichia* sp., preferably *Escherichia coli*.

For purposes of the present invention, antimicrobial activity may be determined according to the procedure described by Lehrer et al., *Journal of Immunological Methods* 137(2): 167-174 (1991). Alternatively, antimicrobial activity may be determined according to the NCCLS guidelines from CLSI (Clinical and Laboratory Standards Institute; formerly known as National Committee for Clinical and Laboratory Standards).

Polypeptides having antimicrobial activity may be capable of reducing the number of living cells of *Escherichia coli* (DSM 1576) to $1/100$ after 24 hours (preferably after 12 hours, more preferably after 8 hours, even more preferably after 4 hours, most preferably after 2 hours, and in particular after one hour) incubation at 37° C. in a relevant microbial growth substrate at a concentration of 500 micrograms/ml; preferably at a concentration of 250 micrograms/ml; more preferably at a concentration of 100 micrograms/ml; even more preferably at a concentration of 50 micrograms/ml; most preferably at a concentration of 25 micrograms/ml; and in particular at a concentration of 10 micrograms/ml of the polypeptides having antimicrobial activity.

Polypeptides having antimicrobial activity may also be capable of inhibiting the outgrowth of *Escherichia coli* (DSM 1576) for 24 hours at 37° C. in a relevant microbial growth substrate, when added in a concentration of 500 micrograms/ml; preferably when added in a concentration of 250 micrograms/ml; more preferably when added in a concentration of 100 micrograms/ml; even more preferably when added in a concentration of 50 micrograms/ml; most preferably when added in a concentration of 10 micrograms/ml; and in particular when added in a concentration of 5 micrograms/ml.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the antimicrobial activity of the polypeptide consisting of the amino acid sequence of SEQ ID NO: 1.

Isolated polypeptide: The term "isolated variant" or "isolated polypeptide" as used herein refers to a variant or a polypeptide that is isolated from a source. In one aspect, the variant or polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment).

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Modification: The term "modification" means herein any chemical modification of the polypeptide consisting of the amino acid sequence of SEQ ID NO: 1 as well as genetic manipulation of the DNA encoding that polypeptide. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus.

Polypeptides having Antimicrobial Activity

In a first aspect, the present invention relates to isolated polypeptides having an amino acid sequence which has a degree of identity to SEQ ID NO: 1 (i.e., the mature polypeptides) of at least 80%, preferably at least 85%, more preferably at least 90%, most preferably at least 95%, and in particular at least 97%, which have antimicrobial activity (hereinafter "homologous polypeptides"). In a preferred aspect, the homologous polypeptides have an amino acid sequence which differs by at the most eight amino acids, preferably by at the most seven amino acids, more preferably by at the most six amino acids, even more preferably by at the most five amino acids, even more preferably by at the most four amino acids, even more preferably by at the most three amino acids, most preferably by at the most two amino acids, and in particular by one amino acid from the amino acid sequence of SEQ ID NO: 1.

In an embodiment, the homologous polypeptides comprise a substitution in position 5 to Ala, Arg, Asn, Asp, Cys, Gln, Glu, Gly, His, Ile, Leu, Lys, Met, Phe, Pro, Ser, Thr, Trp or Val, as compared to SEQ ID NO: 1; such as Tyr5Asn (Y5N) or Tyr5His (Y5H).

In yet another aspect, the polypeptides of the invention has one or several amino acid changes compared to the amino acid sequence of SEQ ID NO: 1.

A polypeptide of the present invention preferably comprises the amino acid sequence of SEQ ID NO: 1 or an allelic variant thereof. In a preferred aspect, a polypeptide comprises the amino acid sequence of SEQ ID NO: 1, SEQ ID NO: 2, or SEQ ID NO: 3. In another preferred aspect, a polypeptide consists of the amino acid sequence of SEQ ID NO: 1, SEQ ID NO: 2, or SEQ ID NO: 3 or an allelic variant thereof. In another preferred aspect, a polypeptide consists of the amino acid sequence of SEQ ID NO: 1, SEQ ID NO: 2, or SEQ ID NO: 3.

Preferably, amino acid changes are of a minor nature, that is conservative amino acid substitutions or insertions that do not significantly affect the folding and/or activity of the polypeptide; single deletions; small amino- or carboxyl-terminal extensions; a small linker peptide of up to about 20-25 residues; or a small extension that facilitates purification by changing net charge or another function, such as a polyhistidine tag, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., antimicrobial activity) to identify amino acid residues that are critical to the activity of the molecule. See also, Hilton et al., 1996, *J. Biol. Chem.* 271: 4699-4708. The biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

N-Terminal Extension

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Kex2 Sites

Kex2 sites (see, e.g., Methods in Enzymology Vol 185, ed. D. Goeddel, Academic Press Inc. (1990), San Diego, Calif., "Gene Expression Technology") and kex2-like sites are dibasic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an antimicrobial polypeptide being extended in comparison to the mature polypeptide shown in SEQ ID NO: 1.

Fused Polypeptides

The polypeptides of the present invention also include fused polypeptides or cleavable fusion polypeptides in which another polypeptide is fused at the N-terminus or the C-terminus of the polypeptide of the invention or a fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Methods and Uses

The invention relates to the use of a polypeptide of the invention for treating urinary tract infections. Accordingly, the polypeptides of the invention may be used as a veterinarian or human therapeutic or prophylactic agent. Thus, polypeptides of the invention may be used for the manufacturing of a medicament for the treatment of urinary tract infections, such as cystitis, for example bacterial cystitis. In an embodiment, urinary tract infections are caused by Gram negative bacteria, such as an uropathogenic strain of *Escherichia coli* (UPEC); preferably a multiple drug resistant *E. coli*.

The polypeptides of the invention may be used in an amount sufficient to kill or inhibit growth of *E. coli*.

Formulations of the polypeptides of the invention are administered to a host suffering from or predisposed to urinary tract infections.

Administration may be localized or systemic. Generally the dose of the antimicrobial polypeptides of the invention will be sufficient to decrease the microbial population by at least 1 log, and may be by 2 or more logs of killing. The polypeptides of the present invention are administered at a dosage that reduces the microbial population while minimizing any side-effects. It is contemplated that the composition will be obtained and used under the guidance of a physician for in vivo use.

Various methods for administration may be employed. The polypeptide formulation may be given orally, or may be injected intravascularly, intramuscular, subcutaneously, intraperitoneally, by aerosol, opthalmically, intra-bladder, topically, etc. The dosage of the therapeutic formulation will vary widely, depending on the specific antimicrobial polypeptide to be administered, the frequency of administration, the manner of administration, the clearance of the agent from the host, and the like. The initial dose may be larger, followed by smaller maintenance doses. In many cases, oral administration will require a higher dose than if administered intravenously. The amide bonds, as well as the amino and carboxy termini, may be modified for greater stability on oral administration. For example, the carboxy terminus may be amidated.

Formulations

The polypeptides of this invention can be incorporated into a variety of formulations for therapeutic administration. More particularly, the polypeptides of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the polypeptides can be achieved in various ways, including oral, buccal, rectal, parenteral, intraperitoneal, intradermal, transdermal, intracheal, etc., administration. The antimicrobial polypeptides of the invention may be systemic after administration or may be localized.

The polypeptides of the present invention can be administered alone, in combination with each other, or they can be used in combination with other known compounds (e.g., perforin, anti-inflammatory agents, antibiotics, etc.) In pharmaceutical dosage forms, the polypeptides may be administered in the form of their pharmaceutically acceptable salts. The following methods and excipients are merely exemplary and are in no way limiting.

For oral preparations, the polypeptides can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The polypeptides can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The polypeptides can be utilized in aerosol formulation to be administered via inhalation. The polypeptides of the present invention can be formulated into pressurized acceptable propellants such as dichlorodifluoromethane, propane, nitrogen and the like.

Furthermore, the polypeptides can be made into suppositories by mixing with a variety of bases such as emulsifying bases or water-soluble bases. The polypeptides of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more polypeptides of the present invention. Similarly, unit dosage forms for injection or intravenous administration may comprise the polypeptide of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of polypeptides of the present invention calculated in an amount sufficient to produce the desired effect in association with a pharmaceutically acceptable diluent, carrier or vehicle. The specifications for the unit dosage forms of the present invention depend on the particular polypeptide employed and the effect to be achieved, and the pharmacodynamics associated with the polypeptide in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific polypeptide, the severity of the symptoms and the susceptibility of the subject to side effects. Some of the specific polypeptides are more potent than others. Preferred dosages for a given polypeptide are readily determinable by those of skill in the art by a variety of means. A preferred means is to measure the physiological potency of a given polypeptide.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al., *J. Biol. Chem.* 266:3361 (1991) may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with other Active Agents

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g., penicillin G, penicillin V, methicillin, oxacillin, carbenicillin, nafcillin, ampicillin, etc.; penicillins in combination with beta-lactamase inhibitors, cephalosporins, e.g., cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g., amphotericin B, nystatin; 5-flucosyn; and azoles, e.g., miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g., interferon gamma, tumor necrosis factor alpha, interleukin 12, etc.

In Vitro Synthesis

The polypeptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g., D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g., reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

The present invention is further described by the following examples that should not be construed as limiting the scope of the invention.

EXAMPLES

Example 1

Treatment of an *E. coli* Urinary Tract Infection

The antimicrobial peptide used in the experiment is a polypeptide having the amino acid sequence shown in SEQ ID NO: 1. In the Example, this polypeptide will be referred to as "Arenicin".

Conclusion

The efficacy of Arenicin (10 mg/kg) (formulated in Ringer acetate pH 6) was investigated following intravenous (i.v.) administration BID day 1 and day 2 post infection. The effect was tested against *Escherichia coli* DSA 443 (clinical isolate, SSI) in a murine Urinary Tract Infection, UTI, model. Treatment with 40 mg/kg Meropenem was included as a positive control group. The colony counts in urine, bladder and kidney were determined on day 3 post infection.

Treatment with Arenicin resulted in a significant bacterial reduction in the urine after 1 day of treatment ($p<0.001$), after 2 days of treatment ($p<0.001$); and in the bladder after 2 days of treatment ($p<0.01$), compared to vehicle (Ringer acetate) treatment. A slight reduction was also observed in the kidneys of mice treated with Arenicin.

The effect of Arenicin was comparable to the effect of the Meropenem, using the chosen experimental dosages.

Background

The purpose of this study was to investigate the efficacy of Arenicin (10 mg/kg) and, following intravenous (i.v.) administration BID days 1 and 2 post infection, tested against *Esherichia coli* DSA443 in a murine UTI model.

*Escherichia coli* DSA 443 is a clinical isolate from blood from 2006. SHV-12. Multiresistant (Ampicillin, Cefuroxim, Ceftazidime, Cefpodoxine, Gentamicin, trimethoprim, sulfamethoxazol, amoxicillin/clav). Serotype $O65:K^-:H^+$, $PGUA^+$ (production of β-glucuronidase, $HLY^-$ (hemolysin), $VCA^-$ (production of verocytotoxin).

Method

The efficacy of Arenicin administered BID i.v. days 1 and 2 post infection at a rate of 10 ml/kg to female OF-1 mice (14/group), at a dosage of 10 mg/kg, was assessed against *E. coli* DSA 443. Treatment with 40 mg/kg Meropenem was included as a positive control and treatment with vehicle was included as a negative control.

Starting on day −4 before inoculation, mice were given drinking water containing 5% glucose. On day 0, the bladder of each mouse was emptied of urine, and each mouse was inoculated with 50 microliters bacteria suspension (*E. coli* DSA 443 9.3 $\log_{10}$ CFU/ml) via a catheter in the urethra into the bladder.

Urine was sampled from all mice at 24 hours post infection, before the first treatment, and colony counts were determined. 48 and 72 hours post infection, urine was sampled from all mice and kept at room temperature until analyzed. CFU was determined in urine samples within 2-3 hours after sampling. On day 3, mice were sacrificed by cervical dislocation and the bladders and kidneys were collected and stored at −80° C. until analyses. Frozen organs were thawed and homogenized with steel beads on a tissue lyser. All samples, urine, kidney and bladder, were 10 fold diluted in saline and 20 microliter spots were applied on blue agar plates in duplicates. Also undiluted urine (100 microliters if possible) was spread on a separate agar plate to determine the colony counts lowest possible detection level (10 CFU/ml). All agar plates were incubated 18-22 hrs at 35° C. in ambient air.

The mice were clinically scored for signs of infection at the time of sampling.

Results

The CFU numbers are $\log_{10}$ transformed before performing calculations to obtain a normal (or closer to normal) distribution. The data are presented below in Table 1 as mean±SEM. Significance levels were calculated with one-way ANOVA, Dunnett's multiple comparison test and are indicated by the stars in the figures.

Immediately before start of treatment the CFU levels in urine were determined in all treatment groups. The CFU levels ranged from 1.7 to 8.4 $\log_{10}$ with a mean of 6.9±1.4 $\log_{10}$. The variation within the groups and between the groups was as expected in this model.

In the vehicle treated mice, the CFU levels in urine remained the same throughout the 3 day study period. Before treatment, day 1 post infection, the CFU level was 6.1±0.7 $\log_{10}$, after one day of treatment, day 2 post infection, the CFU level was 6.1±0.7 $\log_{10}$ and after completed treatment, day 3 post infection the CFU level was 6.5±0.4 $\log_{10}$.

Arenicin treatment significantly ($p<0.001$) reduced the bacterial loads in the urine. Before treatment, day 1 post infection, the CFU level was 6.9±0.3 $\log_{10}$, after one day of treatment, day 2 post infection, the CFU level was 3.2±0.5 $\log_{10}$ and after completed treatment, day 3 post infection the CFU level was 2.3±0.3 $\log_{10}$. The CFU reduction by Arenicin treatment was comparable to that of Meropenem. The effect of Meropenem in this study was as excepted and in accordance with previous studies.

In the bladder the CFU level was 5.7±0.6 $\log_{10}$ in vehicle treated mice day 3 post infection. This is in accordance with what is normally observed in non treated mice in this model. Significant lower ($p<0.01$) CFU levels were seen after treatment with Arenicin as compared to vehicle treated mice. Arenicin treatment resulted in 3.8±0.2 $\log_{10}$ CFU in the bladder. The CFU reduction following treatment with Arenicin was comparable to that of Meropenem. The effect of Meropenem in this study was as excepted and in accordance with previous studies.

During the urinary tract infection, bacteria normally spread to the kidneys in a fraction (30-70%) of the mice. In this study, bacteria were detectable in the kidneys in 7 of 12 mice in the vehicle group which was in accordance with expectations. In the kidneys of vehicle treated mice, the mean CFU level was 2.5±0.4 $\log_{10}$. Arenicin treated mice had similar fraction of infected kidneys but slightly lower mean CFU levels, 1.9±0.3 $\log_{10}$. However, this reduction was not significantly lower than the vehicle group. Similarily, Meropenem treated mice also had slightly, but not significantly, reduced bacterial loads in the kidneys. This was also in line with previous studies where Meropenem consistently has resulted in significant reduction of bacterial loads in urine and bladder, but in the kidneys the reduction is sometimes significant and sometimes only minor with no significance.

TABLE 1

Colony counts of *E. coli* DSA 443 in mice treated with vehicle, Arenicin, Variant1 or Meropenem.

| Mean colony counts + SEM ($\log_{10}$ CFU) | | Treatment | | |
|---|---|---|---|---|
| | | Vehicle | Arenicin (10 mg/kg) | Meropenem (40 mg/kg) |
| Urine | day 1 | 6.1 ± 0.7 | 6.9 ± 0.3 | 7.0 ± 0.4 |
| | day 2 | 6.1 ± 0.7 | 3.2 ± 0.5 *** | 2.7 ± 0.3 *** |
| | day 3 | 6.5 ± 0.4 | 2.3 ± 0.2 *** | 2.1 ± 0.3 *** |
| Bladder | day 3 | 5.7 ± 0.6 | 3.8 ± 0.2 ** | 3.9 ± 0.3 ** |
| Kidney | day 3 | 2.5 ± 0.4 | 1.9 ± 0.3 | 1.8 ± 0.3 |

Significance levels:
** $p < 0.01$,
*** $p < 0.001$.

Example 2

Treatment of an *E. coli* Urinary Tract Infection

In this example, the antimicrobial polypeptide having the amino acid sequence shown in SEQ ID NO: 2 will be referred to as "Variant1". Variant1 includes a Y5N+Y17H substitution as compared to Arenicin (SEQ ID NO: 1).

The antimicrobial polypeptide having the amino acid sequence shown in SEQ ID NO: 3 will be referred to as "Variant2". Variant2 includes a W4G+Y5H substitution as compared to Arenicin.

The experiment was carried out as described in Example 1.

Method and Conclusion

The efficacies of Variant1 and Variant2 (10 mg/kg) (formulated in Ringer acetate pH 6) were investigated following intravenous (i.v.) administration BID day 1 and day 2 post infection with *Escherichia coli* DSA 443 (clinical isolate, SSI) in a murine Urinary Tract Infection model. Treatment with 40 mg/kg Meropenem was included as a positive control group.

Treatment with Variant1 or Variant2 resulted in a significant bacterial reduction in the urine after 2 days of treatment ($p<0.001$); and in the bladder after 2 days of treatment ($p<0.01$), compared to vehicle (Ringer acetate) treatment. A significant bacterial reduction was also observed in the kidneys of mice treated with Variant1 or Variant2 ($p<0.05$).

The effects of treatment with Variant1 or Variant2 were comparable to the effect of treatment with Meropenem, using the chosen experimental dosages.

TABLE 2

Colony counts of *E. coli* DSA 443 in mice treated with vehicle, Variant1, Variant2 or Meropenem.

| Mean colony counts ± SEM ($\log_{10}$ CFU) | | Treatment | | | |
|---|---|---|---|---|---|
| | | Vehicle | Variant1 (10 mg/kg) | Variant2 (10 mg/kg) | Meropenem (40 mg/kg) |
| Urine | day 1 | 6.0 ± 0.8 | 7.1 ± 0.8 | 5.7 ± 1.0 | 6.3 ± 1.0 |
| | day 3 | 5.8 ± 1.1 | 2.6 ± 0.4 *** | 3.2 ± 0.5 *** | 1.8 ± 0.4 *** |
| Bladder | day 3 | 5.3 ± 0.8 | 3.8 ± 0.4 ** | 3.7 ± 0.5 ** | 3.9 ± 0.2 ** |
| Kidney | day 3 | 2.6 ± 0.9 | 1.3 ± 0.2 * | 1.5 ± 0.4 * | 1.8 ± 0.4 |

Significance levels:

\* $p < 0.05$,

\*\* $p < 0.01$,

\*\*\* $p < 0.001$.

The invention claimed is:

1. A method of treating urinary tract infections, comprising administering to a subject in need of such treatment an effective amount of a polypeptide having antimicrobial activity, which consists of an amino acid sequence 21 amino acids in length consisting of at least 90% identity to the amino acid sequence of SEQ ID NO: 1, SEQ ID NO: 2 or SEQ ID NO: 3.

2. The method according to claim 1, wherein the polypeptide consists of an amino acid sequence 21 amino acids in length consisting of at least 95% identity to the amino acid sequence of SEQ ID NO: 1.

3. The method according to claim 1, wherein the polypeptide consists of an amino acid sequence 21 amino acids in length consisting of at least 97% identity to the amino acid sequence of SEQ ID NO: 1.

4. The method according to claim 1, wherein the polypeptide consists of an amino acid sequence 21 amino acids in length consisting of at least 95% identity to the amino acid sequence of SEQ ID NO: 2.

5. The method according to claim 1, wherein the polypeptide consists of an amino acid sequence 21 amino acids in length consisting of at least 97% identity to the amino acid sequence of SEQ ID NO: 2.

6. The method according to claim 1, wherein the polypeptide consists of an amino acid sequence 21 amino acids in length consisting of at least 95% identity to the amino acid sequence of SEQ ID NO: 3.

7. The method according to claim 1, wherein the polypeptide consists of an amino acid sequence 21 amino acids in length consisting of at least 97% identity to the amino acid sequence of SEQ ID NO: 3.

8. The method according to claim 1, wherein the urinary tract infection is cystitis.

9. A polypeptide having antimicrobial activity which consists of an amino acid sequence having at least 95% identity to SEQ ID NO:2 or SEQ ID NO:3.

10. The polypeptide according to claim 9, wherein said polypeptide has at least 97% identity to SEQ ID NO:2 or SEQ ID NO:3.

* * * * *